United States Patent [19]

Bunick et al.

[11] Patent Number: 5,059,441

[45] Date of Patent: Oct. 22, 1991

[54] METHOD FOR MAKING MOLDED PRODUCTS

[75] Inventors: Frank J. Bunick, Randolph; Ahmed A. Soliman, Budd Lake, both of N.J.

[73] Assignee: Warner-Lambert Company, Morris Plains, N.J.

[21] Appl. No.: 418,597

[22] Filed: Oct. 10, 1989

[51] Int. Cl.$^5$ .......................... A23G 1/00; B28B 1/00
[52] U.S. Cl. ..................... 426/515; 264/86; 426/660
[58] Field of Search ............... 426/515, 414, 660; 249/113, 134; 425/84, 85; 264/86, 87

[56] References Cited

U.S. PATENT DOCUMENTS

| | | | |
|---|---|---|---|
| 1,239,167 | 9/1917 | Dickson | 426/660 |
| 1,621,568 | 3/1927 | Vose | 426/660 |
| 3,067,262 | 12/1962 | Brady | 106/10 |
| 3,074,803 | 1/1963 | McGowan et al. | 426/661 |
| 3,130,060 | 4/1964 | Evans | 426/660 |
| 3,226,239 | 12/1965 | Schoch et al. | 127/33 |
| 3,303,052 | 2/1967 | Hatch et al. | 106/38.22 |
| 3,460,606 | 8/1969 | Boddey | 249/134 |
| 3,935,292 | 1/1976 | Okubo et al. | 264/338 |
| 3,958,997 | 5/1976 | Greenburg | 106/38.35 |
| 4,225,627 | 9/1980 | Moore | 426/660 |
| 4,229,484 | 10/1980 | Steels et al. | 426/515 |
| 4,335,147 | 6/1982 | Sollich | 426/660 |
| 4,388,334 | 6/1983 | Deveaux | 426/515 |
| 4,403,932 | 9/1983 | Ogasawara et al. | 425/85 |
| 4,472,339 | 9/1984 | van der Ploeg et al. | 249/113 |
| 4,609,511 | 9/1986 | Fischer et al. | 264/51 |
| 4,867,662 | 9/1989 | Shimahara et al. | 425/85 |

OTHER PUBLICATIONS

Porex Technologies, Technical and Promotional Literature, 10 pages, published in 1988.

*Primary Examiner*—George Yeung
*Attorney, Agent, or Firm*—Craig M. Bell

[57] ABSTRACT

A porous polymer plastic material and apparatus containing same useful for making molds, and particularly molds for casting confectionery, pharmaceutical and cosmetic products, and process for preparing molded products.

25 Claims, No Drawings

METHOD FOR MAKING MOLDED PRODUCTS

BACKGROUND OF THE INVENTION

1. Field of the Invention

The invention relates to the use of a porous polymer plastic to replace the starch molds used in the manufacture of food and non-food products. More particularly the invention covers molds containing a porous polymer plastic, method of making molded products, and products made therefrom.

2. Description of Related Art

Molded products, such as confectionery products are prepared by depositing a fluid mass into a preformed mold, allowing the fluid mass to solidify or gel therein and removing the solidified or gelled product from the mold. Preformed depressions in a bed of dry powdered starch are the most commonly used method.

There have been several recent developments in the molding industry which have attempted to eliminate the use of starch. Starch processing has many drawbacks; the dustiness is an obvious disadvantage and, going along with it, the explosion hazard. The continuous use of starch also creates a microbiological problem for, in spite of the required heating, drying, and sifting, the starch is never sterile, in fact molding starch can have high bacterial counts. Sifting never eliminates all foreign matter and splinters of wood from broken trays and confectionery residues may contaminate the products. In addition rodents can be a serious problem in the base of the machines and can cause further serious contamination.

"Starchless" molding technology has developed from the use of metal molds with compressed air ejection of the pieces. In addition, rubber and silicone rubber molds have been used for some types of fondant, caramels, and toffees. Plastic coated "drop" rolls have also been used for certain cremes and pastes. The starchless molds are usually constructed in a tray form, each of which may contain a hundred or more depressions with the trays being operatively connected with one another to form a continuous belt or conveyor. In a continuous starchless molding operation for soft confections, each mold is typically coated with a special release agent, the fluid confectionery recipe ingredients are then cast or deposited into the starchless mold (depositing), solidified therein (tempering), mechanically ejected therefrom (demolding), cleaned and coated with fresh release agent for recycling. In demolding, the mechanical ejection may be accomplished by mechanical fingers which force the gelled composition from a deformed flexible mold (e.g., molds constructed of synthetic or natural rubber molds) or by air expulsion from a rigid mold. One of the disadvantages with such starchless molding techniques is the cost of preparing and changing molds which is very high resulting in the restricted use of such molds to well established products with assured markets rather than to products being field tested on an experimental basis.

Starchless molding procedures also require maintenance. In a continuous operation, each mold is cleaned so that it is free from solidified confectionery product and microbial contamination before recoating with fresh release agent and recycling. Critical processing factors need to be developed for effective air demolding. These include the size and configuration of the holes within the base of the mold impression, the type of release agent and how it is applied, the mold design and construction, air pressure, cooling time and conditions and so forth.

In this regard, incomplete and non-uniform release of the solidified confectionery product from the mold are particularly troublesome problems since sugar solutions tend to stick to any mold surface. Numerous proposals have been made to improve upon the release of the solidified confectionery product from the mold. In an attempt to overcome these problems, polytetrafluoroethylene is conventionally used as a permanent mold coating. For soft confections, a temporary release agent coating (e.g., acetylated monoglyceride) is necessarily applied before each deposition of confection into the mold.

According to the present invention, the disadvantages of starch molding as well as the additional "starchless molding" techniques have been obviated by the use of a porous polymer plastic which functions similar to starch.

SUMMARY OF THE INVENTION

This invention describes the novel use of a porous polymer plastic, and particularly a hydrophilic porous polymer plastic, to replace the starch used in starch molds during the manufacture of deposited food or non-food products. The use of this porous polymer plastic provides for effective drying of deposited product formulations through the polymer's "wicking" action which draws water or solvent away from the product in a manner similar to starch.

Applicants have unexpectedly discovered a mold composition for forming a moldable product which comprises a mold prepared from a porous polymer plastic material.

Applicants have also unexpectedly discovered a mold forming agent suitable for the production of molded products, which comprises a porous polymer material other than starch.

Another embodiment of the present invention involves a method for making a molded product, which comprises: depositing a fluid mass of product into a porous polymer mold other than starch; gelling, or otherwise setting the fluid mass while absorbing moisture into the porous polymer; and recovering the formed product.

In a preferred embodiment of the invention, Applicants have discovered a method for preparing a molded product, which comprises a) preparing a fluid mass of product ingredients; b) depositing the fluid mass into a solid mold comprising a porous polymer plastic other than starch; c) removing moisture from the product by absorption into the porous polymer; d) gelling, or otherwise setting the fluid mass within the mold to provide a molded product and e) expelling the product from the mold.

DESCRIPTION OF THE PREFERRED EMBODIMENTS

According to the present invention, a novel mold, method for making a molded product and product therefrom has been unexpectedly discovered wherein the mold is prepared from a porous polymer plastic, other than starch.

The use of a porous polymer produce or a material of similar properties will allow starch to be replaced in traditional molding operations. This applies to food items such as confections as well as non-food items such as pharmaceutical and cosmetic products. Thus porous polymers have utility in the processing of a wide variety of produce formulations currently being made by the starch casting technique. The application of porous polymers to wet casting eliminates the problems associated with starch casting such as, explosion hazards, microbial contaminations, messy starch trays and starch dust, and so forth.

Porous polymers can be used when produce formulations are deposited in a molten or fluid sate requiring starch for the removal of excess water or solvent. For molding purposes, the porous polymers can be formed, cut or otherwise shaped into a variety of shapes and sizes. In confectionery applications, a large sheet of polymer would be formed into a mold containing many individual depressions into which a fluid mass is deposited.

Upon cooling, the polymer sheets containing deposited material would be stored under conditions required to complete drying of the product to an appropriate solids level. These conditions might range from ambient to controlled temperature and humidity conditions and may involve passing air over and/or below the porous polymer mold to facilitate removal of moisture from the "wick-like" porous polymer.

As with the techniques used with molding starch, the porous polymer will be used to form the impressions for the deposited product. The impressions may be made on top of existing support frames or structures, such as those presently used in starch molding. In addition to using existing supports, molds may be prepared from the porous polymer itself provided suitable thicknesses are employed. Polymer thicknesses may range from thin coatings on top of supports (several microns thick) to structures having thicknesses from one-sixteenth inch to several inches thick. Preferred structures are self supporting and have thicknesses from about one-eighth to about one-half inch thick.

The products used to fill the mold should be in a molten or fluid state, that is either pourable into the mold or capable of being compressed by the mold. Such products usually contain from about 5 to about 85% by total weight of water or solvent. Once placed or compressed by the mold, the product will be left in the mold for a sufficient time to permit the water or solvent to wick-into the porous polymer. This wicking action results in a drying effect causing the product to gel and/or harden. Suitable times will vary depending upon the product being made and the amount of water or solvent that needs to be removed. Exemplary times may range from 15 minutes to several days and preferably for at least 1 to 24 hours.

Unlike new starch which does not print well and requires the addition of mineral or vegetable oil to improve bonding, the porous polymers used in the present invention may be employed without such additives. The porous polymers form a mold which has a smooth surface resulting in products having a smooth surface and which can be easily removed from the mold.

It is also known that starch molds need to be aerated. The mold board which prints the impressions compresses the starch in the tray. If the starch is too dense, it compacts badly and prevents deep mold impressions. Aeration is normally done after passing the starch through a fine sieve.

Unlike starch, the porous polymer plastic once compressed into the mold need not be replaced following each molding operation. This thus enables the molds to be reused multiple times without concern about mold depth and cleaning. In addition, the porous polymers are capable of being aerated, like starch molds, so that moisture or solvent picked up by the mold is easily removed. Such aeration procedures may entail passing air over and/or below the polymer plastic to remove entrapped solvent or moisture.

The use of the present porous polymer plastic also eliminates the need to remove the tailings and fragments of deposited products that is required in starch molding procedures. In addition, the present porous polymer molds do not require heat to remove the moisture or solvent from the product as is required when using rubber or metal molds which must be heated to high temperatures to form a solid product.

It should also be evident that the porous polymer molding of this invention avoids the dust, explosion hazards and microbial contaminations present with starch molding operations. Furthermore, porous polymer molding allows the use of traditional starch cast formulations where other starchless systems require formula modifications or special ingredients.

The porous polymers useful in the present invention comprise those polymers which are capable of wicking solvent or water from a product to be molded. Exemplary polymers include synthetically produced plastic polymers and particularly those which may be selected from the group consisting of high-density polyethylene, high molecular weight polyethylene, polypropylene, ethylene-vinyl acetate, polytetrafluoroethylene, styrene-acrylonitrile, polyvinylidene fluoride, mixtures thereof and the like.

The porous polymers are preferably hydrophilic in character and have an average pore size of 0.8 to 2000 micrometers. Depending on the material to be molded and the substance to be removed by wicking a specific polymer material may be selected to achieve maximum product hardening within the shortest time period. For example, when removing solvent from a cosmetic or pharmaceutical composition a pore size of about 35 to 500 micrometers have been found to be useful. Suitable material having this pore size may be obtained from high-density polyethylene (having an average pore size of 35 to greater than 250 micrometers) and polypropylene (having an average pore size from 125 to 350 micrometers). In contrast, when removing water from a product such as confectionery product, pore sizes of from about 5 to 100 have been found suitable. Such pore sizes can be obtained using high molecular weight polyethylene (having an average pore size from 10 to 40 micrometers) and the above mentioned materials. Products having this pore size and porous structure may be obtained from Porex Technologies, USA.

Any product which is capable of being prepared in a starch mold may be prepared in the molds of this invention. While not being limited to particular products a wide variety of confectionery, pharmaceutical and cosmetic products may be prepared using the porous polymer molds of this invention. Exemplary pharmaceutical and cosmetic products include tableted and molded products, stick deodorants, suppositories, lip-stick, shaped cosmetic products and so forth.

The confectionery material may be selected from the group consisting of fondant creams, jellies, nut pastes, marzipans, turkish delights, soft caramels, fudges, marshmallows, gums and pastilles as well as other confectionery products that may be compressed and/or molded such as shaker molded products.

A preferred process for performing the molding procedure involves depositing a molten or fluid mass of product into the porous polymer mold; gelling or hardening the molten fluid mass by absorbing moisture or solvent in the porous polymer; and recovering the formed product.

A particularly preferred procedure for preparing the molded product, comprises preparing a molten or fluid mass of product ingredients, depositing the fluid into a solid mold comprising the porous polymer plastic, removing moisture from the product by absorption into the porous polymer, gelling or hardening the fluid mass within the mold to provide a molded product and expelling the product from the mold.

Moisture or solvent may be removed by evaporation into the surrounding atmosphere or by passing air over and/or below the polymer mold to accelerate the procedure.

It should be appreciated that the mold may contain one or more port holes for air or steam injection to remove the product once formed. As in conventional operations, the present molds may employ standard ejection procedures, such as the use of pressure being applied to the bottom of the mold to force the product out of the mold or compressed air or steam which passes through tiny holes in the bottom of each mold while they are tilted at an inverted angle, usually 45°. Critical processing factors for affecting pressure, air or steam demolding are well within the skill of the ordinary skilled artisan and do not constitute a part of this invention.

In addition to the use of ejection means, the molds of the invention may be equipped with cooling means which circulate within the mold to aid in chilling the material to be hardened. Such means are well known for chocolate coating confectionery products.

The following examples serve to provide further appreciation of the invention but are not meant in any way to restrict the effective scope of the invention. All percentages throughout the specification are by weight % of the final product unless otherwise indicated and wherein all percentages will total 100% of ingredients in the final composition.

EXAMPLE

This example compares the loss of moisture from a deposited product when added to various molds.

A cooked gelatin solution (containing about 75% solids and about 25% water) was placed into three separate molds having identical configurations. The amount of moisture loss was measured (by weight measurements) over a fifty five hour period. The results indicate that moisture loss from mold A prepared from polyvinylchloride was significant lower than that achieved for molds containing the inventive polyethylene porous polymer (B) and conventional starch mold (C).

The invention being thus described, it will be obvious that the same may be varied in many ways. Such variations are not to be regarded as a departure from the spirit and scope of the invention and all such modification are intended to be included within the scope of the following claims.

We claim:

1. A method for making a molded product consisting essentially of depositing a molten or fluid mass of substantially dissolved product into a porous hydrophilic polymer mold; gelling or hardening the fluid mass while absorbing moisture or solvent into the porous polymer mold by a wicking action and recovering the formed product.

2. The method of claim 1, wherein the fluid mass of product contains from about 5% to about 85% water.

3. The method of claim 1, wherein the fluid mass of product contains from about 5% to about 85% solvent.

4. The method of claim 1, wherein the produce is a food or non-food item.

5. The method of claim 4, wherein the product is a confectionery material.

6. The method of claim 4, wherein the product is a pharmaceutical product or cosmetic product.

7. The method of claim 1, wherein the porous polymer is selected from the group consisting of high-density polyethylene, high molecular weight polyethylene, polypropylene, ethylene-vinyl acetate, polytetrafluoroethylene, styrene-acrylonitile, polyvinylidene fluoride, and mixtures thereof.

8. The method of claim 7, wherein the porous polymer has an average pore size of 0.8 to 2000 micrometers.

9. The method of claim 1, wherein air is passed over the porous polymer mold to facilitate removal of moisture or solvent from the porous polymer.

10. The method of claim 1 wherein air is passed under the porous polymer mold to facilitate removal of moisture or solvent from the porous polymer.

11. The method of claim 1 wherein the gelled or hardened product has a consistency ranging from a pliable plastic mass to a pliable solidified mass.

12. The method of claim 5, wherein the confectionery material is selected from the group consisting of fondant cremes, jellies, nut pastes, marzipans, turkish delights, soft caramels, fudges, marshmallows, gum and pastilles.

13. A method of preparing a molded product consisting essentially of:
   (a) preparing a fluid mass of substantially dissolved product ingredients;
   (b) depositing the fluid mass into a solid mold comprising a porous hydrophilic polymer plastic;
   (c) removing moisture or solvent from the product by a wicking action into the porous polymer mold;
   (d) gelling or solidifying the fluid mass within the mold to provide a molded product; and
   (e) expelling the product from the mold.

14. The method of claim 13, wherein the fluid mass of product contains from about 5% to about 85% water.

15. The method of claim 13, wherein the fluid mass of product contains from about 5% to about 85% solvent.

16. The method of claim 13, wherein the product is a food or non-food item.

17. The method of claim 16, wherein the product is a confectionery material.

18. The method of claim 16, wherein the product is a pharmaceutical product or cosmetic product.

19. The method of claim 13, wherein the porous polymer mold is a hydrophilic material.

20. The method of claim 13, wherein the porous polymer is selected from the group consisting of high-density polyethylene, high molecular weight polyethylene, polypropylene, ethylene-vinyl acetate, polytetrafluoroethylene, styrene-acrylonitile, polyvinylidene fluoride and mixtures thereof.

21. The method of claim 20, wherein the porous polymer has an average pore size of 0.8 to 2000 micrometers.

22. The method of claim 13, wherein air is passed over the porous polymer mold to facilitate removal of moisture from the porous polymer.

23. The method of claim 13 wherein air is passed under the porous polymer mold to facilitate removal of moisture from the porous polymer.

24. The method of claim 13 wherein the gelled or hardened product has a consistency ranging from a pliable plastic mass to a pliable solidified mass.

25. The method of claim 17, wherein the confectionery material is selected from the group consisting of fondant cremes, jellies, nut pastes, marzipans, turkish delights, soft caramels, fudges, marshmallows, gums and pastilles.

* * * * *